United States Patent
Fujiwara et al.

(10) Patent No.: US 10,814,055 B2
(45) Date of Patent: Oct. 27, 2020

(54) DIALYSIS-FLUID SUPPLY SYSTEM

(71) Applicant: NIKKISO CO., LTD., Tokyo (JP)

(72) Inventors: Masato Fujiwara, Higashimurayama (JP); Yoshimichi Masuda, Higashimurayama (JP); Hiroshi Nimura, Higashimurayama (JP)

(73) Assignee: NIKKISO CO., LTD., Tokyo (JP)

( * ) Notice: Subject to any disclaimer, the term of this patent is extended or adjusted under 35 U.S.C. 154(b) by 0 days.

(21) Appl. No.: 15/524,495

(22) PCT Filed: Nov. 12, 2015

(86) PCT No.: PCT/JP2015/081855
§ 371 (c)(1),
(2) Date: May 4, 2017

(87) PCT Pub. No.: WO2016/080279
PCT Pub. Date: May 26, 2016

(65) Prior Publication Data
US 2017/0312413 A1    Nov. 2, 2017

(30) Foreign Application Priority Data

Nov. 20, 2014    (JP) .................................. 2014-235457

(51) Int. Cl.
*A61M 1/16*      (2006.01)
*A61M 1/36*      (2006.01)
(Continued)

(52) U.S. Cl.
CPC ........... *A61M 1/1666* (2014.02); *A61K 31/19* (2013.01); *A61K 33/00* (2013.01); *A61K 33/14* (2013.01);
(Continued)

(58) Field of Classification Search
CPC .......................... A61M 1/168; A61M 2209/10
See application file for complete search history.

(56) References Cited

U.S. PATENT DOCUMENTS 4,134,834 A    1/1979   Brous
5,972,223 A *   10/1999   Jonsson ................ A61L 2/0023
                                                   137/88

(Continued)

FOREIGN PATENT DOCUMENTS

EP          0714668 A1    6/1996
JP          S55-047863 A   4/1980
(Continued)

OTHER PUBLICATIONS

JP2004041742A (EPO Machine Translation) (Year: 2018).*
(Continued)

*Primary Examiner* — Patrick Orme
(74) *Attorney, Agent, or Firm* — Oliff PLC

(57) ABSTRACT

This dialysis-fluid supply system, which mixes a diluent and at least two drugs to generate a dialysis fluid, and outputs said dialysis fluid, is provided with: two tanks which mix the drugs and the diluent to generate the dialysis fluid, and store said dialysis fluid; a water supply device and a drug supply device which supply the diluent and the drugs to each of the tanks; mechanisms for outputting, to a dialysis device, the dialysis fluid stored in each of the tanks; and a control unit for controlling the driving of these. During output of the dialysis fluid from at least one of the tanks, the control unit sequentially switches the supply destination tank for the drugs and the diluent, and the dialysis-fluid output source tank, between the two tanks in order to generate the dialysis fluid in the other tank.

10 Claims, 5 Drawing Sheets

(51) Int. Cl.
*A61K 31/19* (2006.01)
*A61K 33/00* (2006.01)
*A61K 33/14* (2006.01)

(52) U.S. Cl.
CPC .......... *A61M 1/168* (2013.01); *A61M 1/1656* (2013.01); *A61M 1/1668* (2014.02); *A61M 1/3692* (2014.02); *A61M 2205/3379* (2013.01); *A61M 2205/3382* (2013.01); *A61M 2205/3386* (2013.01); *A61M 2205/3393* (2013.01); *A61M 2209/10* (2013.01)

(56) References Cited

U.S. PATENT DOCUMENTS

| | | | | |
|---|---|---|---|---|
| 2004/0211718 | A1* | 10/2004 | Deguchi | A61M 1/1656 210/252 |
| 2008/0230450 | A1 | 9/2008 | Burbank et al. | |
| 2013/0189376 | A1* | 7/2013 | Carlsson | A61K 9/0029 424/678 |

FOREIGN PATENT DOCUMENTS

| | | | | |
|---|---|---|---|---|
| JP | H05-034988 | B2 | | 5/1993 |
| JP | H08-080345 | A | | 3/1996 |
| JP | H09-000618 | A | | 1/1997 |
| JP | 11033109 | A | * | 2/1999 |
| JP | H11-033109 | A | | 2/1999 |
| JP | 2004-041742 | A | * | 2/2004 |
| JP | 2004-041742 | A | | 2/2004 |
| JP | 2007-117396 | A | * | 5/2007 |
| JP | 2008-168078 | A | | 7/2008 |
| JP | 2008-526375 | A | | 7/2008 |

OTHER PUBLICATIONS

JP2007117396 (EPO Machine Translation) (Year: 2018).*
JPH1133109A (EPO Machine Translation) (Year: 2018).*
Jun. 7, 2018 Extended European Search Report issued in Patent Application No. 15861342.2.
English Translation of the Mar. 2, 2017 International Preliminary Report on Patentability issued in Patent Application No. PCT/JP2015/081855.
Feb. 2, 2016 International Search Report issued in Patent Application No. PCT/JP2015/081855.
Aug. 25, 2020 Office Action issued in Chinese Patent Application No. 201580062841.8.

* cited by examiner

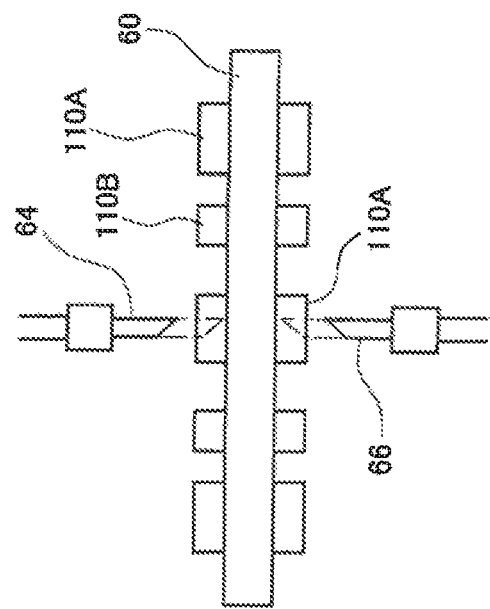
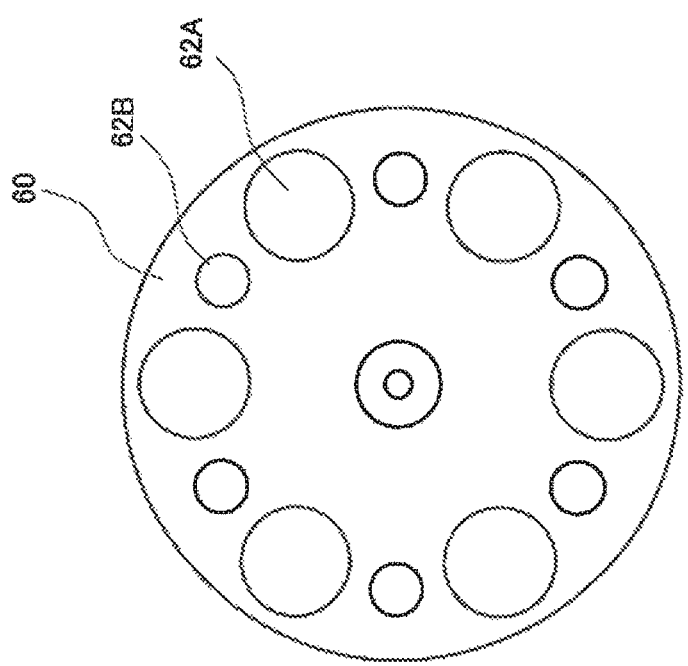
FIG. 4A
FIG. 4B

DIALYSIS-FLUID SUPPLY SYSTEM

TECHNICAL FIELD

The present invention relates to a dialysis-fluid supply system that generates dialysis fluid by mixing a diluent and at least two drugs, and outputs the dialysis fluid.

BACKGROUND ART

In a conventionally known dialysis-fluid supply system, a plurality of drugs and a diluent (for example, water) are mixed together to generate and output dialysis fluid. Widely known examples of the dialysis-fluid supply system include a dialysis-fluid continuous supply system that generates dialysis fluid by continuously mixing a plurality of drugs and a diluent. The dialysis-fluid continuous supply system requires a measurement pump capable of accurately measuring the amounts of a diluent and a drug concentrated solution transferred for mixing. However, such a measurement pump capable of performing accurate measurement is typically expensive and requires frequent maintenance.

To avoid this problem, in a batch system, the drugs and the diluent in amounts necessary for achieving a desired concentration are collectively supplied to a tank to generate dialysis fluid instead of continuously generating dialysis fluid. Patent Literatures 1 and 2 disclose such dialysis-fluid batch supply systems. In the batch system, drugs and the like are measured in advance, or measurement means is provided to the tank, which eliminates the need to provide an accurate measurement pump. This leads to further reduction in the price of the dialysis-fluid supply system and also in the amount of maintenance work.

CITATION LIST

Patent Literature

Patent Literature 1: National Publication of International Patent Application No. 2008-526375
Patent Literature 2: Japanese Patent Laid-Open Publication No. Hei 9-618
Patent Literature 3: U.S. Pat. No. 4,134,834

SUMMARY OF INVENTION

Technical Problem

However, the dialysis-fluid supply system disclosed in Patent Literature 1 is intended to employ lactic acid dialysis fluid used in peritoneal dialysis, but not bicarbonate dialysis fluid widely used in blood dialysis treatment nowadays. The dialysis-fluid supply system disclosed in Patent Literature 2 is intended to employ bicarbonate dialysis fluid, but can be used for dialysis treatment in a relatively short time (for example, two hours). Specifically, bicarbonate dialysis fluid is generated by mixing a diluent and two kinds of drugs called drugs A and B. However, when a certain time (for example, two hours) has elapsed after the mixing of the drugs A and B, a deposit is generated in this bicarbonate dialysis fluid, and the bicarbonate dialysis fluid can no longer be used in blood dialysis treatment. Thus, in the technology of Patent Literature 2, in which dialysis fluid is generated in one tank, the dialysis fluid can be output only in an amount that can be used up within this certain time, and dialysis fluid in excess of that amount cannot be output. However, a continuous dialysis treatment over a longer time (for example, six hours) is required depending on the condition and lifestyle of a patient, and such a requirement by the patient cannot be sufficiently met by the technology of Patent Literature 2.

Patent Literature 3 discloses a system including two tanks. In the system, while one of the tanks outputs dialysis fluid, the other tank generates dialysis fluid, and when the one tank runs out of the dialysis fluid, the other tank outputs the dialysis fluid while the one tank generates dialysis fluid. However, the dialysis-fluid supply system of Patent Literature 3 is not intended to employ bicarbonate dialysis fluid. Moreover, the dialysis-fluid supply system of Patent Literature 3 includes a measurement pump to measure a diluent, resulting in an expensive system that requires frequent maintenance work.

It is an advantage of the present invention to provide a dialysis-fluid supply system that generates and outputs dialysis fluid obtained by mixing a plurality of drugs, and is inexpensive and capable of outputting a larger amount of the dialysis fluid.

Solution to Problem

A dialysis-fluid supply system according to the present invention is a dialysis-fluid supply system that generates dialysis fluid by mixing a diluent and at least two drugs and outputs the dialysis fluid. The dialysis-fluid supply system includes: at least two tanks that each generate dialysis fluid by mixing the drugs and the diluent and stores the dialysis fluid; a supply mechanism that supplies the drugs and the diluent to each of the tanks; an output mechanism that outputs the dialysis fluid stored in each of the at least two tanks to a dialysis device; and a control unit that controls driving of the supply mechanism and the output mechanism. While the dialysis fluid is output from at least one of the tanks, the control unit switches, between the tanks in turn, a tank to which the drugs and the diluent are supplied by the supply mechanism, and a tank from which the dialysis-fluid is output by the output mechanism to generate dialysis fluid in the rest of the tanks.

In a preferable aspect, the tank may include at least a weight sensor that measures the weight of supplied fluid or a level sensor that measures the level of supplied fluid, and the control unit may control the driving of the supply mechanism based on a result of detection by the weight sensor or the level sensor.

In another preferable aspect, the dialysis-fluid supply system may further include a circulation mechanism that internally and externally circulates fluid inside the at least two tanks to perform agitation. In another preferable aspect, the dialysis-fluid supply system may further include a return line that returns, to the supply mechanism, fluid output from one tank, and the control unit may execute a cleaning process of supplying cleaning fluid into the tank to clean the tank, and may supply cleaning fluid supplied to and discharged from at least one of the tanks, as cleaning fluid to another tank through the return line.

In another preferable aspect, having switched a tank from which the dialysis fluid is output, the control unit may discard the dialysis fluid remaining in a tank that was switched from and any line coupled with the tank. In another preferable aspect, the supply mechanism may include a drug supply mechanism that supplies the at least two drugs to a tank, the drug supply mechanism may be configured to switch a tank to which the at least two drugs are supplied, and one drug supply mechanism may supply the drugs to at least two tanks.

Advantageous Effects of Invention

In a dialysis-fluid supply system according to the present invention, a tank to which drugs and a diluent are supplied and a tank from which dialysis fluid is output are switched between at least two tanks in turn, which allows continuous supply of dialysis fluid generated a short time before. The dialysis-fluid supply system according to the present invention is a batch supply system in which drugs and a diluent are collectively supplied to a tank to generate dialysis fluid, which eliminates the need to provide an expensive measurement pump that requires maintenance work. Accordingly, an inexpensive dialysis-fluid supply system capable of outputting a larger amount of dialysis fluid can be provided.

BRIEF DESCRIPTION OF DRAWINGS

FIG. 4(a) is a schematic plan view of a turntable provided on a drug supply device,
and
FIG. 4(b) is a schematic configuration diagram of the drug supply device.

DESCRIPTION OF EMBODIMENT

Figure 1:
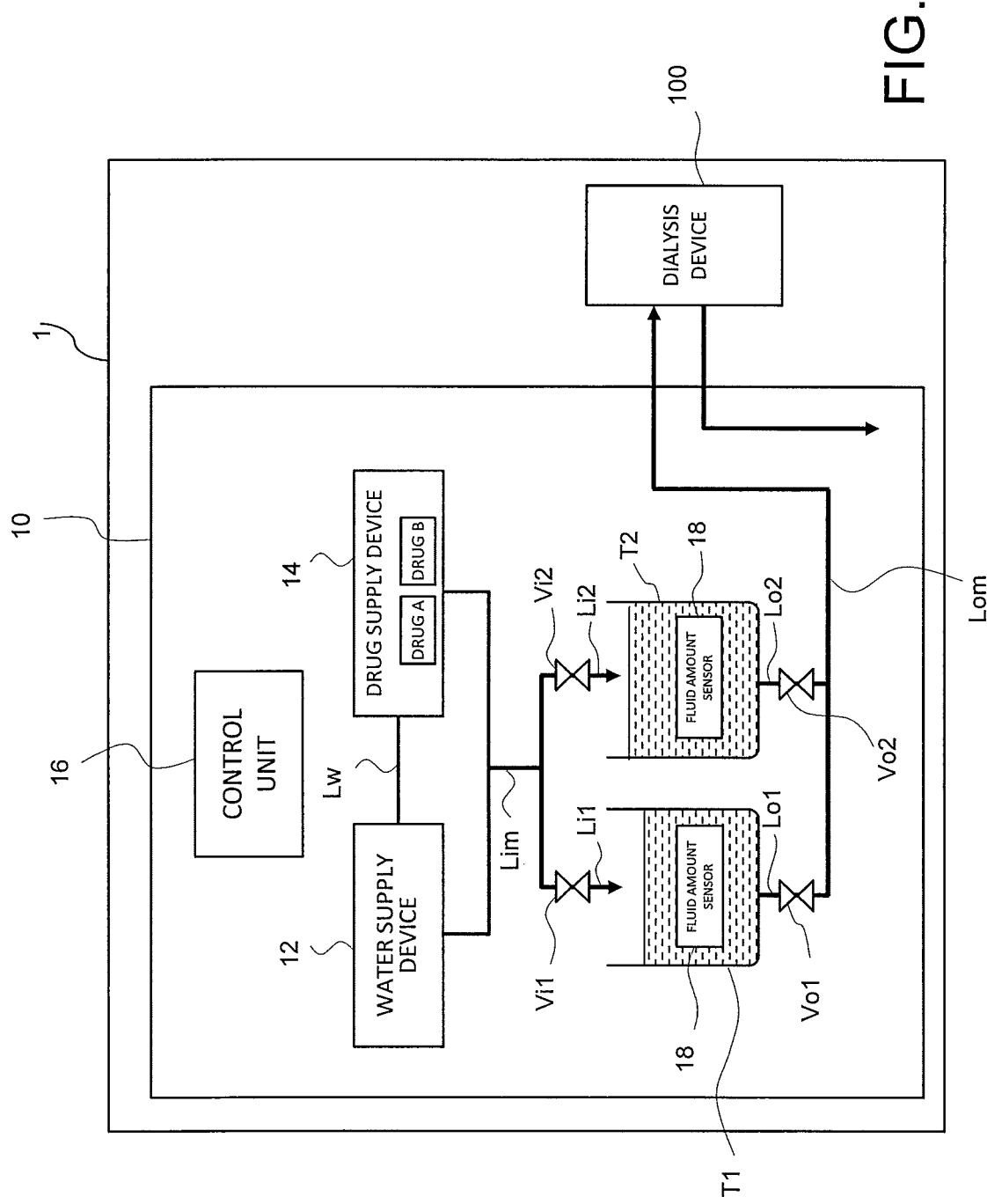
FIG. 1 is a diagram illustrating the configuration of a dialysis system according to a basic embodiment of the present invention.

The following describes a dialysis system 1 according to an embodiment of the present invention with reference to the accompanying drawings. FIG. 1 is a diagram illustrating a basic embodiment of the present invention. The dialysis system 1 illustrated in FIG. 1 includes a dialysis-fluid supply system 10 and a dialysis device 100 connected with the dialysis supply system 10. The dialysis device 100 cleans blood by circulating the blood out of the body of a patient through a blood circulating system including a dialyzer that cleans blood by allowing blood and dialysis fluid to come in to contact with each other through a semipermeable membrane, an arterial blood circuit that takes in blood from the patient and inputs the blood to the dialyzer, and a venous blood circuit that returns, to the patient, blood output from the dialyzer; a dialysis-fluid supplying and discharging system including lines that supply and discharge the dialysis fluid to and from the dialyzer; and a blood pump provided in the arterial blood circuit. The dialysis-fluid supply system 10 generates dialysis fluid by mixing a diluent and a plurality of drugs, and supplies the generated dialysis fluid to the dialysis device 100.

The dialysis system 1 has a relatively small-sized configuration suitable for medical treatment of a small number (for example, one) of patients, and is expected to be used in a relatively small-sized facility such as a hospital or a home but not in a dialysis clinic. However, the number of tanks T1 and T2 to be described later and the capacities thereof can be changed to provide a configuration suitable for simultaneous medical treatment of a large number of patients and use at a large-sized facility. The dialysis-fluid supply system 10 and the dialysis device 100 are preferably integrated to achieve reduction in the size of the entire system, but may be separated.

The dialysis-fluid supply system 10 mainly includes a plurality (in the present example, two) of the tanks T1 and T2, a supply mechanism that supplies a drug and a diluent to the tanks T1 and T2, an output mechanism that outputs dialysis fluid stored in the tanks T1 and T2 to the dialysis device 100, and a control unit 16 that controls driving of the supply mechanism and the output mechanism.

The supply mechanism includes a water supply device 12 that supplies water as the diluent, a drug supply device 14 that supplies a drug A and a drug B, input lines Lim, Li1, and Li2 connected with these devices, and a plurality of valves Vi1 and Vi2 provided on the input lines Li1 and Li2, respectively. The water supply device 12 may have, but is not particularly limited to, any configuration capable of supplying highly pure water. Thus, the water supply device 12 may be, for example, an RO device 52 that generates highly pure RO water by removing impurities from water through a reverse osmosis membrane (RO membrane), or a water treatment device that generates highly pure water through ion exchange resin and an ultrafiltration membrane (UF membrane). The water supply device 12 supplies water to the tanks T1 and T2 and the drug supply device 14 through the lines Lw, Lim, Li1, and Li2.

The drug supply device 14 supplies the drugs of the dialysis fluid to the tanks T1 and T2. In the present embodiment, the dialysis fluid is bicarbonate dialysis fluid. The bicarbonate dialysis fluid is, as is well known, obtained by mixing and diluting two kinds of drugs, which are the drugs A and B. The drug A includes an electrolyte component (for example, sodium chloride, potassium chloride, calcium chloride, magnesium chloride, or sodium acetate), a pH adjuster (for example, acetic acid), and sugar (for example, glucose). The drug B includes sodium bicarbonate. The drugs A and B are set in the drug supply device 14 in advance and supplied to the tanks T1 and T2 together with water. The drugs A and B set to the drug supply device 14 are desirably individually packaged in advance in an amount necessary for each generation of the dialysis fluid. When the dialysis-fluid supply system 10 includes a mechanism for measuring the drugs A and B, however, the drugs A and B do not need to be measured and packaged in advance.

The drugs A and B set in the drug supply device 14 may be provided in powder form or tablet form, or may be provided as concentrated solution dissolved with a small amount of diluent. Alternatively, one of the drugs A and B set in the drug supply device 14 may be in liquid form, and the other may be in solid form (powder form or tablet form). The drug supply device 14 may supply the drugs A and B set in powder form or tablet form directly to the tanks T1 and T2, or may supply the drugs A and B to the tanks T1 and T2 as a concentrated solution dissolved with a small amount of water. In any case, the drug supply device 14 only needs to supply a necessary amount of the drugs of the dialysis fluid to the tanks T1 and T2. In the present embodiment, the bicarbonate dialysis fluid is exemplarily described, but the dialysis fluid may be any other kind of dialysis fluid generated by mixing and diluting a plurality of drugs.

The water from the water supply device 12 and the drugs from the drug supply device 14 are output to the main input line Lim. The main input line Lim bifurcates into the first input line Li1 connected with the first tank T1, and the second input line Li2 connected with the second tank. The first and second input lines Li1 and Li2 are provided with the first and second input valves Vi1 and Vi2, respectively, opening and closing of which are driven by the control unit 16. Tanks to which the water and the drugs are supplied, in other words, tanks for processing of generating dialysis fluid, can be switched by switching the opening and closing of the input valves Vi1 and Vi2.

The tanks T1 and T2 are containers that generate dialysis fluid by mixing and diluting the water and the drugs, and store the generated dialysis fluid. In the present embodiment, the first and second tanks T1 and T2 are provided as two tanks having an identical configuration.

The concentration of the bicarbonate dialysis fluid changes due to generation of a deposit when a certain time elapses after mixing of the drugs A and B, and thus a time duration in which the bicarbonate dialysis fluid is usable after its generation, in other words, a use limit time duration is set. The use limit time duration differs slightly between kinds of product, but is typically approximately two hours. In the present embodiment, the tanks T1 and T2 have capacities equal to or less than the amount of dialysis fluid used in dialysis treatment in the use limit time duration. For example, when the use limit time duration is two hours and the flow rate of dialysis fluid used in dialysis treatment is 500 mL/min, the tanks T1 and T2 have capacities equal to or less than 500 mL×120 min=60 L. Since consideration needs to be given to such a problem that a time duration until a deposit is generated from when the drugs A and B are mixed changes with solution temperature and the like, and depending on a time duration in which the dialysis fluid is stored after production, the use limit time duration is preferably set to be one hour to reliably prevent a deposit. In this case, when the flow rate of dialysis fluid is 500 mL/min, the tanks T1 and T2 desirably have capacities equal to or less than 500 mL×60 min=30 L. When the flow rate of dialysis fluid is 250 mL/min, the tanks T1 and T2 desirably have capacities equal to or less than 250 mL×60 min=15 L.

The tanks T1 and T2 each include a fluid amount sensor 18 that detects the amount of supplied fluid, such as a level switch that detects a fluid level, or a load sensor that detects the weight of supplied fluid. In addition, the tanks T1 and T2 each desirably include a concentration sensor (not illustrated) that detects the concentration of the dialysis fluid generated and stored in the tanks T1 and T2. In the present embodiment, the number of tanks is two, but a larger number of tanks may be provided.

The dialysis fluid stored in the tanks T1 and T2 is output to the dialysis device 100 through output lines Lom, Lo1, and Lo2, respectively. The first and second output lines Lo1 and Lo2 are connected with the first and second tanks T1 and T2, respectively, and join together to be the main output line Lom. The dialysis fluid is output to the dialysis device 100 through the main output line Lom. The first and second output lines Lo1 and Lo2 are provided with first and second output valves Vo1 and Vo2, respectively, opening and closing of which are driven by the control unit 16. A tank from which the dialysis fluid is output can be switched by switching the opening and closing of the first and second output valves Vo1 and Vo2. Accordingly, the output lines Lom, Lo1, and Lo2 and the output valves Vo1 and Vo2 function as the output mechanism that outputs the dialysis fluid stored in the tanks T1 and T2 to the dialysis device 100.

Figure 2:
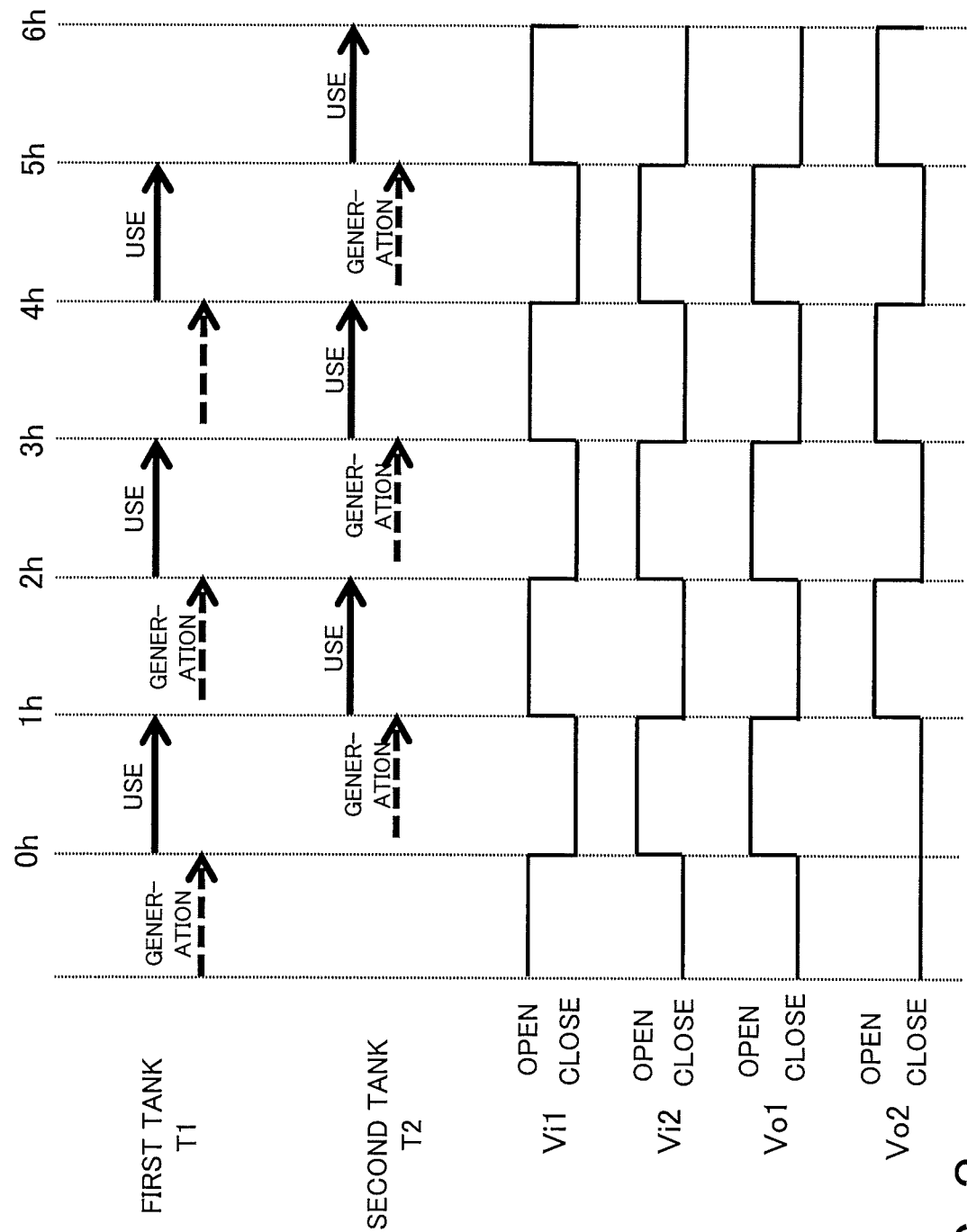
FIG. 2 is a timing chart illustrating timings of switching between tanks and opening and closing of various valves in a dialysis-fluid supply system in FIG. 1.

The control unit 16 controls driving of the water supply device 12, the drug supply device 14, and the various valves Vi1, Vi2, Vo1, Vo2, and the like described above. In the present embodiment, the control unit 16 switches the opening and closing of the various valves to switch the tanks T1 and T2 between generation of dialysis fluid and outputting of dialysis fluid in turn. FIG. 2 is a timing chart illustrating timing of the switching of the tanks T1 and T2 and the opening and closing of the various valves Vi1, Vi2, Vo1, and Vo2 in the dialysis-fluid supply system 10.

As illustrated in FIG. 2, the control unit 16 first opens the first input valve Vi1 (High in FIG. 2) and closes the other valves Vi2, Vo1, and Vo2 to generate dialysis fluid in the first tank T1. Having generated the dialysis fluid, the first tank T1 outputs the dialysis fluid, and the second tank T2 generates dialysis fluid. In this case, the first input valve Vi1 and the second output valve Vo2 are closed, and the first output valve Vo1 and the second input valve Vi2 are opened. Once the dialysis fluid in the first tank T1 is completely used, the second tank T2 outputs the dialysis fluid, and the first tank T1 generates new dialysis fluid. In this case, the first output valve Vo1 and the second input valve Vo2 are closed, and the first input valve Vi1 and the second output valve Vo2 are opened. Subsequently, the same processing is repeated while the tanks are alternately switched between outputting and generation of dialysis fluid.

As described above, in the present embodiment, the plurality (in the embodiment, two) of the tanks T1 and T2 are provided and switched between generation and outputting of dialysis fluid in turn. This configuration is provided for the following reason.

Conventionally, in most dialysis-fluid supply systems, dialysis fluid is continuously generated and supplied. Specifically, in the conventional dialysis-fluid supply system, concentrated solutions of the drugs A and B and water are accurately measured by a measurement pump, and then supplied into a line and mixed through the line to generate dialysis fluid at a desired concentration. Such a dialysis-fluid continuous supply system requires a measurement pump capable of accurately measuring the amount of fluid and transferring the fluid. However, typically, such a measurement pump is extremely expensive and needs frequent maintenance, and thus is difficult to install at a small sized facility.

To solve this difficulty, a dialysis-fluid batch supply system has been proposed in which certain amounts of drugs and water are supplied to a tank to generate dialysis fluid. In such a dialysis-fluid batch supply system, when the tank includes a fluid amount sensor, no measurement pump is needed, thereby achieving reduction in the price of the entire system and also in amount of maintenance work. However, only one tank that generates dialysis fluid is provided in the conventional dialysis-fluid batch supply system. Thus, the system could not generate a large amount of dialysis fluid.

As described above, the use limit time duration is set for the bicarbonate dialysis fluid. When the bicarbonate dialysis fluid is generated in one tank beyond the use limit time duration, the dialysis fluid that has not been used in the use limit time duration is discarded. Thus, in a configuration in which dialysis fluid is generated in one tank only, that amount of the dialysis fluid in excess of an amount used in medical treatment in the use limit time duration (two hours approximately) cannot be output. Accordingly, when a dialysis-fluid supply system provided with one tank only is employed, a dialysis treatment can be continuously performed in a time duration less than the use limit time duration.

However, a dialysis treatment is continuously performed in a longer time duration depending on the condition and lifestyle of a patient. In particular, it has been desired to reduce the frequency of dialysis treatment by performing the dialysis treatment for a long time (for example, six hours) while the patient is sleeping. However, the conventional dialysis-fluid supply system provided with only one tank could not sufficiently meet such a demand by patients.

To solve this problem, in the present embodiment, as described above, two tanks are provided and switched between generation and outputting of dialysis fluid in turn. With such a configuration, dialysis fluid generated during the use limit time duration can be continuously output. Accordingly, the freedom of medical treatment time can be increased in accordance with the condition and lifestyle of a patient. In the present embodiment, since the tanks T1 and T2 each include the fluid amount sensor 18, no measurement pump needs to be employed as a pump that transfers, for example, water, which leads to reduction in the price of the entire system and also in the amount of maintenance work.

Figure 3:
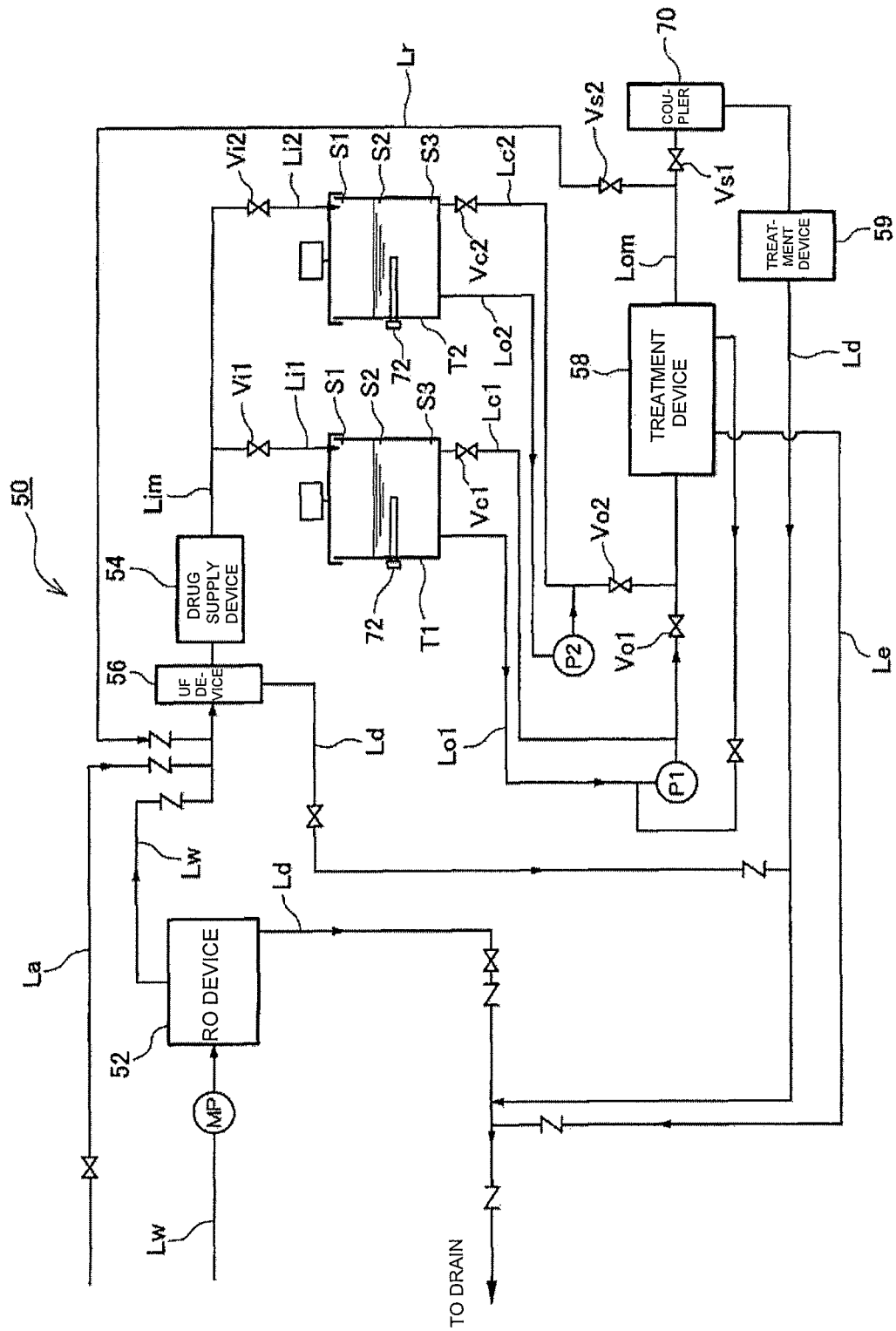
FIG. 3 is a pipe system diagram of a dialysis system according to another embodiment.

The following describes a more specific embodiment with reference to FIGS. 3 and 4. FIG. 3 is a pipe system diagram of a dialysis-fluid supply system 50, and FIG. 4 is a diagram illustrating the configuration of a drug supply device 54 used in the dialysis-fluid supply system 50.

Similarly to the basic embodiment illustrated in FIG. 1, the dialysis-fluid supply system 50 includes the RO device 52 as a water supply device, the drug supply device 54, the first and second tanks T1 and T2, the input lines Lim, Li1, and Li2, and the output lines Lom, Lo1, and Lo2.

The RO device 52 is connected with a water supply source such as a water pipe through the water supply line Lw, and the water supply line Lw is provided with an RO pressurization pump MP. RO water output from the RO device 52 is supplied to the drug supply device 54 through an UF device 56. Waste solution generated through generation of the RO water and waste solution generated through filtration at the UF device 56 are discharged to a drain through a waste solution line Ld.

The drug supply device 54 outputs the RO water supplied from the RO device 52 to the main input line Lim alone or together with the drugs A and B of dialysis fluid. The main input line Lim bifurcates into the first input line Li1 and the second input line Li2 at a halfway point. A tank to which the drugs and the like are supplied is switched between the tanks T1 and T2 by switching opening and closing of the first and second input valves Vi1 and Vi2 provided in the first and second input lines Li1 and Li2, respectively.

The drug supply device 54 individually supplies the drugs A and B of dialysis fluid to the tanks T1 and T2. The following describes the drug supply device 54 with reference to FIG. 4. FIG. 4(a) is a schematic plan view of the drug supply device 54, and FIG. 4(b) is a schematic configuration diagram of a turntable. As illustrated in FIG. 4, the drug supply device 54 according to the present embodiment includes a turntable 60 on which a plurality of drugs (the drugs A and B) are set, and nozzles 64 and 66 capable of contacting with and separating from the drugs set on the turntable 60. The drugs A and B are each individually packaged in an amount used in each generation of dialysis fluid. The turntable 60 is provided with a plurality of set holes 62A and 62B arranged at equal intervals in the circumferential direction. Drug containers 110A and 110B including individual packages of the drugs A and B are set in the set holes 62A and 62B.

An upstream nozzle 64 and a downstream nozzle 66 are disposed on sides of the turntable 60. The nozzles 64 and 66 are each capable of contacting with and separating from the drug containers 110A and 110B set to the turntable 60. The nozzles 64 and 66 have leading ends sharp enough to penetrate into the drug containers 110A and 110B through wall surfaces of the drug containers 110A and 110B. The upstream nozzle 64 is coupled with the water supply line Lw, and the downstream nozzle 66 is coupled with the main input line Lim.

When the drug A or the drug B encapsulated in the drug containers 110A and 110B is transferred to the main input line Lim, the upstream and downstream nozzles 64 and 66 are moved toward the drug containers 110A and 110B to penetrate through the wall surfaces of the drug containers 110A and 110B. In this state, the RO water flows from the upstream nozzle 64 to the downstream nozzle 66 to cause the drug A or the drug B inside the drug containers to flow to the main input line Lim together with the RO water. Once the drugs with a certain amount of the RO water flow to the main input line Lim, supply of the RO water is stopped, and the upstream and downstream nozzles 64 and 66 are separated from the drug containers 110A and 110B. Then, the turntable 60 is rotated so that the next drug containers 110A and 110B are positioned between the upstream and downstream nozzles 64 and 66. Thereafter, the same procedure is repeated to sequentially transfer the drugs A and B to the main input line Lim and thus to the first tank T1 or the second tank T2.

In the present embodiment, the drugs are all output to the main input line Lim, and thereafter the opening and closing of the input valves Vi1 and Vi2 are switched to switch a tank to which the drugs are output. In other words, in the present embodiment, the single drug supply device 54 supplies the drugs to the plurality of tanks T1 and T2. In this manner, only the single drug supply device 54 is provided irrespective of the number of the tanks T1 and T2, thereby preventing increase in the number of components and the size and cost of the entire system.

The first and second tanks T1 and T2 are containers having an identical structure. The tanks T1 and T2 each have a maximum capacity equal to the amount of dialysis fluid used in a dialysis treatment for one hour. For example, when the flow rate of dialysis fluid used in a dialysis treatment is 500 mL/min, the tanks T1 and T2 each have a maximum capacity of 500 mL×60 min=30 L. This tank capacity may be changed in accordance with the flow rate of dialysis fluid. For example, when the flow rate of dialysis fluid used in a dialysis treatment is 250 mL/min, the tanks T1 and T2 each have a maximum capacity equal to or less than 250 mL×60 min=15 L. Production of dialysis fluid needs to take at least 15 minutes to prevent stay of the drugs due to insufficient dissolution, and thus the tanks T1 and T2 desirably have capacities equal to or more than the amount of dialysis fluid used in a dialysis treatment for 15 minutes. Specifically, the tanks T1 and T2 desirably have capacities equal to or more than 7.5 L when the flow rate of dialysis fluid is 500 mL/min, or capacities equal to or more than 3.75 L when the flow rate of dialysis fluid is 250 mL/min.

The tanks T1 and T2 each include, as fluid amount sensors that detect the amount of fluid, three level switches S1 to S3 of an upper limit switch S1, a lower limit switch S3, and a middle switch S2. The upper limit switch S1 detects that the amount of fluid inside the tank T1 or T2 has reached the maximum capacity of the tank. The lower limit switch S3 detects that the amount of fluid inside the tank T1 or T2 has reached an amount recognized to be effectively zero. The middle switch S2 detects that the amount of fluid inside the tank T1 or T2 has reached a middle amount determined in advance. Based on detection signals from the three level switches S1 to S3, the control unit 16 manages a supply amount of the RO water, switches between the tanks T1 and T2 from which dialysis fluid is output, and the like. More specifically, when dialysis fluid is generated, the control unit 16 first supplies the RO water to the tank T1 or T2 until the middle switch S2 is turned on. Subsequently, the drugs A and B are supplied to the tank together with the RO water. Thereafter, the RO water is supplied until the upper limit switch S1 is turned on to generate dialysis fluid at a desired concentration. In outputting dialysis fluid from the tank T1 or T2, when the lower limit switch S3 is turned on, it is recognized that the amount of the dialysis fluid inside one of the tanks T1 and T2 is substantially zero, and the outputting of the dialysis fluid from the one of the tanks T1 and T2 is stopped to output dialysis fluid from the other one of the tanks T1 and T2.

Dialysis fluid stored in the first and second tanks T1 and T2 is output to the dialysis device through the first and second output lines Lo1 and Lo2, respectively, the main output line Lom, and a coupler 70. Circulation pumps P1 and P2 and the output valves Vo1 and Vo2 are provided in the first and second output lines Lo1 and Lo2, respectively. A tank from which dialysis fluid is output is switched between the tanks T1 and T2 by switching opening and closing of the output valves Vo1 and Vo2.

The first and second output lines Lo1 and Lo2 join together to be the main output line Lom at a final stage. Dialysis fluid flowing through the main output line Lom is output to the coupler 70 through a treatment device 58 that performs, for example, temperature adjustment and vapor-liquid separation, flow rate measurement, and concentration measurement of the dialysis fluid. Any exhaust generated during the vapor-liquid separation is discharged to the drain through an exhaust line Le.

A return line Lr is connected with the main output line Lom right before the coupler 70. The return line Lr returns to the water supply line Lw. Switching valves Vs1 and Vs2 are installed in each of the return line Lr and the main output line Lom. A destination of fluid flowing through the main output line Lom is switched between the coupler 70 and the return line Lr by switching opening and closing of the switching valves Vs1 and Vs2. The return line Lr is used to return, for example, cleaning fluid and rinsing water used to clean one of the tanks T1 and T2, for cleaning and rinsing of the other tank. When a plurality of tanks such as the tanks T1 and T2 are provided, for example, the amount of cleaning fluid used to clean the tanks increases with the number of the tanks. However, in the present embodiment, part of, for example, cleaning fluid used for one of the tanks T1 and T2 is returned to the other tank through the return line Lr, which significantly reduces the amount of fluid used for, for example, cleaning of the tanks T1 and T2. The cleaning fluid (for example, hypochlorous water) is supplied through a cleaning fluid line La.

Waste solution output from the dialysis device and waste solution (for example, cleaning fluid after cleaning treatment) output from the tanks T1 and T2 are discharged to the drain through a treatment device 59 that performs blood leakage detection and flow rate measurement, and the waste solution line Ld.

The two tanks T1 and T2 are further coupled with circulation lines Lc1 and Lc2. The circulation lines Lc1 and Lc2 bifurcate from the output lines Lo1 and Lo2, respectively, before returning to the tanks T1 and T2. To dissolve the drug (the drug A or the drug B), the circulation pumps P1 and P2 are driven to circulate the fluid inside the tanks T1 and T2 while circulation valves Vc1 and Vc2 provided in the circulation lines Lc1 and Lc2, respectively, are opened, and the output valves Vo1 and Vo2 are closed. When the fluid inside the tanks T1 and T2 is circulated in this manner, the drug can be more reliably dissolved in a shorter time.

When the RO water and the drugs are supplied to one of the tanks T1 and T2 to generate new dialysis fluid, a slight amount of previously generated dialysis fluid remains in the first output line Vo1 or the second output line Vo2. When this old dialysis fluid is left inside the first output line Vo1 or the second output line Vo2, a deposit is generated in the old dialysis fluid, which results in a change in the concentration of dialysis fluid. When being output to the dialysis device, the dialysis fluid at the changed concentration causes an abrupt change in concentration, which is not desired. In the present embodiment, however, when newly generated dialysis fluid is circulated through the output line Lo1 and the circulation line Lc1, or through the output line Lo2 and the circulation line Lc2, the newly generated dialysis fluid is mixed with any previously generated old dialysis fluid remaining in the output line Lo1 or Lo2 to achieve uniform concentration, thereby significantly reducing the change in concentration.

In the present embodiment, when new dialysis fluid is to be generated, any old dialysis fluid remaining in the tanks T1 and T2 and the output lines Lo1 and Lo2 may be discard in advance instead of circulating the fluid inside the tanks T1 and T2. In this case, the circulation processing of the fluid inside the tanks T1 and T2 may be omitted. When the circulation processing is omitted, however, it is expected that a longer time would be taken to dissolve the drugs and it would be difficult to achieve uniform concentration. Thus, in such a case, it is desirable to provide a separate device for promoting the dissolution and achieving uniform concentration, such as an agitation device that rotates inside the tanks T1 and T2 to agitate the fluid inside, a vibration device that applies vibration to the tanks T1 and T2, or a heating device that heats the tanks T1 and T2 to promote the dissolution.

Figure 5:
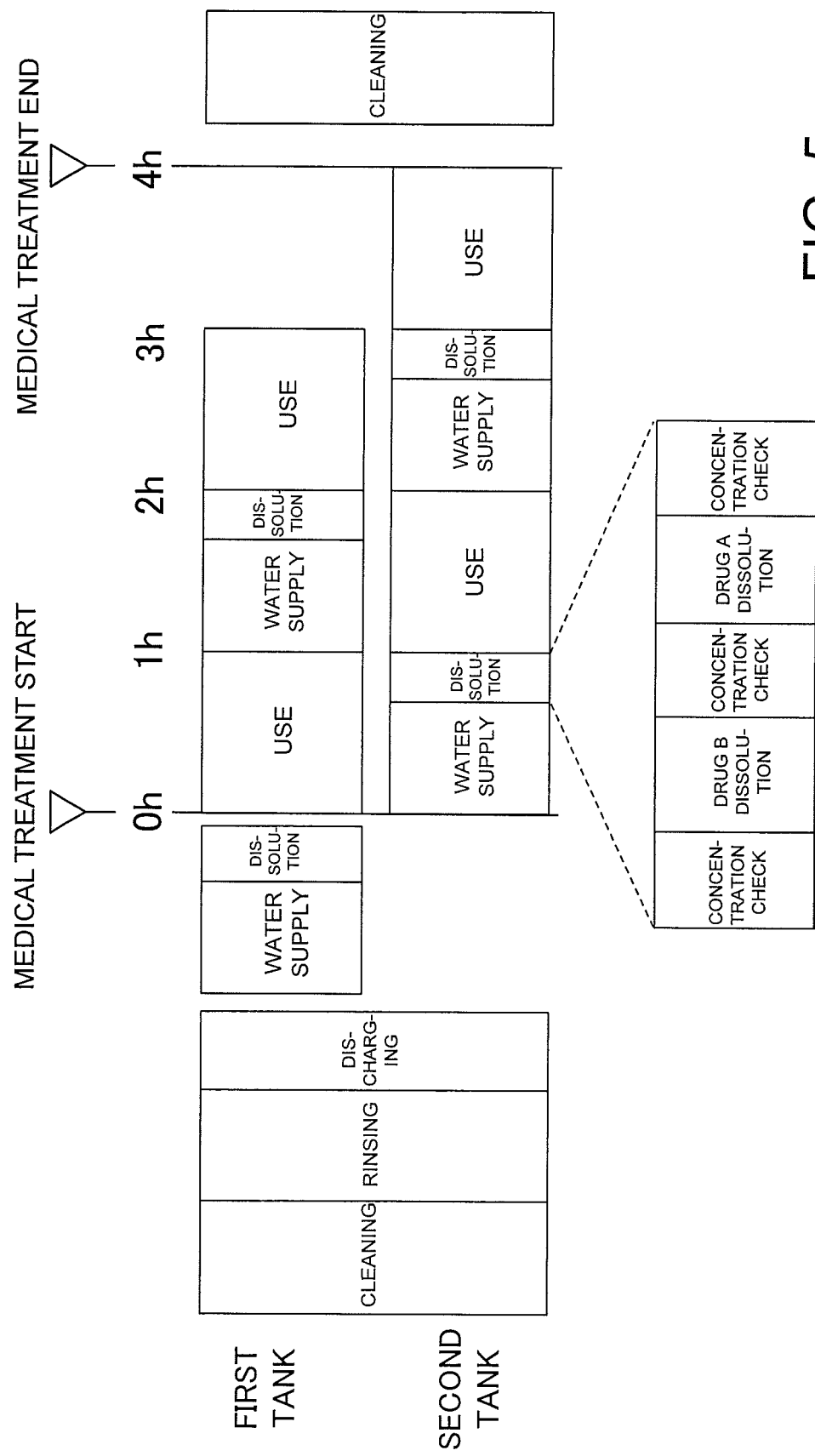
FIG. 5 is a timing chart illustrating timing of processing at a dialysis-fluid supply system in FIG. 4.

The following describes the process of dialysis processing in the above-described device with reference to FIG. 5. FIG. 5 is a timing chart illustrating processing when a dialysis treatment is performed for four hours at the flow rate of dialysis fluid 500 mL/min.

When the dialysis treatment is performed, first, cleaning fluid (for example, hypochlorous water) is supplied to the first and second tanks T1 and T2 to clean the first and second tanks T1 and T2. Subsequently, the RO water as rinsing water is supplied to the first and second tanks T1 and T2 to rinse the first and second tanks T1 and T2. Then, lastly, the rinsing water used in the rinsing is discharged. As described above, the cleaning fluid and the rinsing water used in the cleaning and rinsing may be output, as necessary, from one of the tanks T1 and T2 to the return line Lr and supplied to the other tank for cleaning and rinsing.

Once the cleaning of the first and second tanks T1 and T2 is completed, the first tank T1 subsequently starts generating dialysis fluid. Specifically, first, the RO water is supplied to the first tank T1 until the middle switch S2 is turned on. When the RO water is supplied up to a middle level in the first tank T1, dissolution of the drugs is subsequently started. In the dissolution processing of the drugs, first, a concentration sensor 72 checks the concentration of the fluid inside the tank T1. If there is no problem with the concentration, subsequently, the drug B is supplied to the tank T1 together with the RO water. Once the drug B is supplied to the tank T1 together with a predetermined amount of the RO water, the circulation pump P1 is driven to circulate and agitate the fluid inside the tank T1, thereby dissolving the drug B. After the circulation and agitation for a predetermined time, the concentration of the fluid inside the tank T1 is checked by the concentration sensor 72 to check whether the drug B is dissolved. If there is no problem with the concentration, subsequently, the drug A is supplied to the tank T1 together with the RO water. This supply of the RO water is performed until the upper limit switch S1 is turned on. Then, the circulation pump P1 is again driven to circulate and agitate the fluid inside the tank T1, thereby dissolving the drug A. After the circulation and agitation for a predetermined time, the concentration of the fluid inside the tank T1 is checked by the concentration sensor 72 to check whether the drug A is dissolved. If there is no problem with concentration, it is determined that the dissolution of the drugs is completed, and the first tank T1 starts outputting dialysis fluid.

Simultaneously with the outputting of the dialysis fluid by the first tank T1, the second tank T2 starts generating dialysis fluid. The generation of the dialysis fluid in the second tank T2 is performed in a procedure that is the same as that of the first tank T1.

When the level of the dialysis fluid in the first tank T1 has reached a lower limit level and the lower limit switch S3 has been turned on, the outputting of the dialysis fluid from the first tank T1 is stopped, to start outputting of the dialysis fluid from the second tank T2. Then, simultaneously with the outputting of the dialysis fluid from the second tank T2, the first tank T1 generates new dialysis fluid. Thereafter, the same procedure is repeated until a medical treatment for a necessary time is completed. Once the medical treatment for a necessary time is completed, the first and second tanks T1 and T2 are lastly cleaned to end the present process.

As described above, in the present embodiment, the generation and outputting of dialysis fluid are switched in turn similarly to the dialysis-fluid supply system 10 illustrated in FIG. 1, which allows continuous supply of dialysis fluid generated during the use limit time duration. The amount of fluid is measured by using the level switches S1 to S3 provided in the tanks T1 and T2, which eliminates the need to provide an expensive measurement pump that requires maintenance work, and thus reduction can be achieved in the price of the dialysis-fluid supply system 50 and also in maintenance work.

In the present embodiment, the circulation pumps P1 and P2 and the circulation lines Lc1 and Lc2 are provided to circulate fluid inside the tanks T1 and T2, thereby achieving faster drug dissolution and effectively preventing non-uniform concentration. In addition, in the present embodiment, the return line Lr is provided to return fluid output from the tanks T1 and T2 to upstream of the tanks T1 and T2, which allows sharing of, for example, cleaning fluid used in cleaning and rinsing between the two tanks T1 and T2, and achieves significant reduction in consumption of, for example, the cleaning fluid.

The above-described configuration is merely exemplary. Modifications of the configuration are possible as appropriate to achieve a configuration in which at least a plurality of tanks are provided and generation and outputting of dialysis fluid are switched between the tanks in turn. In the above-described embodiments, fluid inside the tanks T1 and T2 agitated by being internally and externally circulated . However, the agitation is not limited to this method but may be performed by another method. For example, a bladed wheel for agitation may be provided in each tank to perform the agitation.

REFERENCE SIGNS LIST

1 Dialysis system
10, 50 Dialysis-fluid supply system
12 Water supply device
14, 54 Drug supply device
16 Control unit
18 Fluid amount sensor
52 RO device
58, 59 Treatment device
60 Turntable
64 Upstream nozzle
66 Downstream nozzle
70 Coupler
72 Concentration sensor
100 Dialysis device
110A, 110B Drug container
T1, T2 Tank
La Cleaning fluid line
Lc1, Lc2 Circulation line
Ld Waste solution line
Le Exhaust line
Li1, Li2, Lim Input line
Lo1, Lo2, Lom Output line
Lr Return line
Lw Water supply line
MP Pressurization pump
P1, P2 Circulation pump
S1, S2, S3 Level switch
Vc1, Vc2 Circulation valve
Vi1, Vi2 Input valve
Vo1, Vo2 Output valve
Vs1, Vs2 Switching valve

The invention claimed is:
1. A personal dialysis-fluid supply system for use in a medical treatment of one patient that generates dialysis fluid by mixing a diluent and at least two drugs, and outputs the dialysis fluid, the system comprising:
at least two tanks that each generate dialysis fluid by mixing the at least two drugs and the diluent, the at least two tanks storing the mixed dialysis fluid, each of the at least two drugs being in powder form and individually packaged in an amount necessary for a single generation of the dialysis fluid, prior to use;
a supply mechanism that supplies the at least two drugs and the diluent to each of the at least two tanks, the supply mechanism including a drug supply device including a holder configured to hold the at least two drugs and at least two nozzles configured to supply each of the at least two drugs through connection lines to the at least two tanks, the drug supply device being configured to supply all of the at least two drugs that are individually packaged and assigned to a first tank of the at least two tanks to which the drugs and the diluent are supplied, without measuring the at least two drugs;
a first input valve and a second input valve respectively disposed in the connection lines between the drug supply device and each of the at least two tanks, the first input valve and the second input valve being configured to respectively control the supply of the at least two drugs from the drug supply device to a corresponding tank of the at least two tanks without a measurement pump;
an output mechanism that outputs the dialysis fluid stored in each of the at least two tanks through a single main output line to a dialysis device; and
a control unit configured to:
control the first input valve and the second input valve to supply a predetermined amount of each of the at least two drugs from the drug supply device to each of the at least two tanks, control the output mechanism to output the dialysis fluid from at least one of the at least two tanks to the single main output line, and alternately switch between each of the at least two tanks in turn by controlling the supply mechanism to stop supply of the drugs and the diluent to the first tank of the at least two tanks to which the drugs and the diluent are supplied and start supply of the drugs and the diluent to a second tank of the at least two tanks from which the dialysis fluid is output by the output mechanism, while controlling the output mechanism to stop outputting the dialysis fluid from the second tank and start outputting the dialysis fluid from the first tank of the at least two tanks.

2. The dialysis-fluid supply system according to claim 1, wherein:

each tank includes at least a weight sensor that measures a weight of supplied fluid, or a level sensor that measures a level of supplied fluid, and the control unit is configured to control the supply mechanism based on a result of detection by the weight sensor or the level sensor.

3. The dialysis-fluid supply system according to claim 1, further comprising a circulation mechanism that internally and externally circulates fluid inside the at least two tanks to perform agitation.

4. The dialysis-fluid supply system according to claim 1, further comprising a return line that returns, to the supply mechanism, fluid output from the first tank, wherein the control unit is configured to execute a cleaning process of supplying cleaning fluid into each tank to clean the respective tank, and supply the cleaning fluid supplied to and discharged from at least one of the tanks, as cleaning fluid to another tank through the return line.

5. The dialysis-fluid supply system according to claim 1, wherein, upon switching from the first tank to the second tank, the control unit is configured to control at least one output valve to discharge the dialysis fluid remaining in the first tank and any line coupled with the first tank.

6. The dialysis-fluid supply system according to claim 1, wherein:

the control unit is configured to control the drug supply device to switch the supply of the at least two drugs between the first tank and the second tank such that the drug supply device is configured to supply the at least two drugs to either tank.

7. The dialysis-fluid supply system according to claim 1, wherein:

the output mechanism is configured to output an amount of dialysis fluid generated in a single generation process in each tank equal to or greater than B×A and equal to or smaller than C×A, based on (i) a flow rate of the dialysis fluid used is A L/min, (ii) a time duration necessary for the generation process is B min, and (iii) a use limit time duration of the dialysis fluid is C min.

8. The dialysis-fluid supply system according to claim 1, wherein:

the output mechanism is configured to output the dialysis fluid stored in each of the at least two tanks directly to a single dialysis device and not through a storage tank; and the control unit is configured to switch between the first tank to which the drugs and the diluent are supplied and the second tank from which the dialysis fluid is output, after completion of generation of the dialysis fluid in the first tank to which the drugs and the diluent are supplied while a small amount of the dialysis fluid generated in a previous generation process remains in the second tank from which the dialysis fluid is output, to allow the dialysis fluid to be output continuously.

9. The dialysis-fluid supply system according to claim 1, wherein the supply mechanism includes:

a turntable configured to retain the at least two drugs; and an upstream nozzle and a downstream nozzle of the at least two nozzles disposed around a periphery of the turntable, the upstream nozzle and the downstream nozzle being configured to contact and separate from individual packages of the at least two drugs retained by the turntable and cause the at least two drugs to be supplied to the a respective one of the at least two tanks, the downstream nozzle being coupled to a single main input line.

10. A personal dialysis-fluid supply method for use in a medical treatment of one patient that generates dialysis fluid by mixing a diluent and at least two drugs, and outputs the dialysis fluid, the method comprising:

generating dialysis fluid by mixing the at least two drugs and the diluent in one of at least two tanks, the at least two tanks storing the mixed dialysis fluid, each of the at least two drugs being in powder form and individually packaged in an amount necessary for a single generation of the dialysis fluid, prior to use;

supplying, by a supply mechanism, the at least two drugs and the diluent to each of the at least two tanks, the supply mechanism including a drug supply device including a holder configured to hold the at least two drugs and at least two nozzles configured to supply each of the at least two drugs through connection lines to the at least two tanks, the drug supply device being configured to supply all of the at least two drugs that are individually packaged and assigned to a first tank of the at least two tanks to which the drugs and the diluent are supplied, without measuring the at least two drugs;

controlling, by a first input valve and a second input valve, the supply of a predetermined amount of each of the at least two drugs from the drug supply device to a corresponding tank of the at least two tanks without a measurement pump, the first input valve and the second input valve being respectively disposed in the connection lines between the drug supply device and each of the at least two tanks;

outputting, by an output mechanism, the dialysis fluid stored in each of the at least two tanks through a single main output line to a dialysis device; and alternately switching between each of the at least two tanks in turn by controlling the supply mechanism to stop supply of the drugs and the diluent to the first tank of the at least two tanks to which the drugs and the diluent are supplied and start supply of the drugs and the diluent to a second tank of the at least two tanks from which the dialysis fluid is output by the output mechanism, while controlling the output mechanism to stop outputting the dialysis fluid from the second tank and start outputting the dialysis fluid from the first tank of the at least two tanks.

* * * * *